United States Patent [19]
Gates et al.

[11] Patent Number: 5,834,314
[45] Date of Patent: Nov. 10, 1998

[54] METHOD AND APPARATUS FOR METERING A FLUID

[75] Inventors: James D. Gates, Gurnee; Jeffrey Y. Pan, Lake Forest; Tung-Ming Huang, Buffalo Grove; Donald Ver Lee, Libertyville; Alan J. Alcock, Mundelein; Conan K. N. Li, Livertyville; Karen A. Egan, Gurnee, all of Ill.

[73] Assignee: Abbott Laboratories, Abbott Park, Ill.

[21] Appl. No.: 907,143

[22] Filed: Aug. 6, 1997

Related U.S. Application Data

[63] Continuation of Ser. No. 334,902, Nov. 7, 1994, abandoned.

[51] Int. Cl.⁶ .......................... G01N 35/08; G01N 35/10
[52] U.S. Cl. .............................. 436/52; 422/81; 422/82; 422/100; 436/53
[58] Field of Search ............................... 422/81, 82, 100; 436/52, 53

[56] References Cited

U.S. PATENT DOCUMENTS

| | | | |
|---|---|---|---|
| 2,842,400 | 7/1958 | Booth et al. . | |
| 3,083,943 | 4/1963 | Stewart, Jr. et al. | 251/61 |
| 3,286,977 | 11/1966 | Miottel | 251/46 |
| 3,477,693 | 11/1969 | Bezanis | 251/251 |
| 3,600,953 | 8/1971 | Mamaroneck et al. | 422/81 |
| 3,740,019 | 6/1973 | Kessell et al. | 251/129 |
| 3,749,353 | 7/1973 | Pauliukonis | 251/61.1 |
| 3,756,459 | 9/1973 | Bannister et al. | 422/81 |
| 3,934,611 | 1/1976 | Gachot et al. | 137/603 |
| 3,951,167 | 4/1976 | Howell et al. | 137/608 |
| 4,002,269 | 1/1977 | Negersmith | 422/82 |

(List continued on next page.)

FOREIGN PATENT DOCUMENTS

| | | |
|---|---|---|
| 420296A1 | 3/1991 | European Pat. Off. . |
| 931031 | 2/1948 | France . |
| 931540 | 2/1948 | France . |
| 2558922 | 1/1984 | France . |
| 3813925 | 11/1988 | Germany . |

OTHER PUBLICATIONS

Branebjerg, Jens and Peter Gravesen. "A New Electrostatic Actuator providing improved Stroke length and Force". IEEE Micro Electro Mechanical Systems '92, Travelmünde, Germany, feb. 4–7, 1992, pp. 6–11.

Huff, Michael A. et al. "A Pressure–Balanced Electrostatically–Acutated Microvalve". IEEE Solid–State Sensor and Actuator Workshop, Technical Digest, Hilton Head, S.C., Jun. 4–7, 1990, pp. 123–127.

Huff, Michael A. et al. "A Threshold Pressure Switch Utilizing Plastic Deformation of Silicon". IEEE 91CH2817–5/91/0000–0177, 1991, pp. 177–180.

Jensen, D.F. "Pneumatic Digital Control of a Synchronous Device". *Fluidics Quarterly* vol 1 No 1, 1967, pp. 27–37.

(List continued on next page.)

*Primary Examiner*—Jan Ludlow
*Attorney, Agent, or Firm*—Mark C. Bach

[57] ABSTRACT

Embodiments disclosed involve methods and constructions for metering, and in some instances combining, fluids. One such method includes fluidly connecting a source of first fluid to be metered with a pressure source capable of moving the first fluid with a first valve and a conduit. The first valve is operated such that first fluid moves in the conduit. The conduit is fluidly connected with a source of second fluid that has a fluid flow rate greater than the first fluid with a second valve. The second valve is operated such that the second fluid moves into the conduit. One construction for metering a fluid comprises a source of first fluid to be metered, a pressure source for moving the first fluid to be metered, and a first valve. A conduit fluidly connects the source of first fluid, the pressure source for moving the first fluid and the first valve such that operation of the first valve causes movement of the first fluid responsive to the pressure source. A second valve fluidly connects a source of second fluid that has a fluid flow rate greater than the first fluid with the conduit such that operation of the second valve causes movement of the second fluid into the conduit.

12 Claims, 4 Drawing Sheets

U.S. PATENT DOCUMENTS

| | | | |
|---|---|---|---|
| 4,070,004 | 1/1978 | Friswell | 251/331 |
| 4,119,120 | 10/1978 | Mehaffy et al. | 137/885 |
| 4,148,610 | 4/1979 | Miller, Jr. et al. | 422/81 |
| 4,168,724 | 9/1979 | Graffunder et al. | 137/606 |
| 4,239,494 | 12/1980 | Clements . | |
| 4,259,291 | 3/1981 | Smythe | 422/82 |
| 4,304,257 | 12/1981 | Webster | 137/559 |
| 4,353,243 | 10/1982 | Martin | 73/23.1 |
| 4,399,362 | 8/1983 | Cormier et al. | 250/430 |
| 4,479,762 | 10/1984 | Bilstad et al. | 417/395 |
| 4,517,302 | 5/1985 | Saros . | |
| 4,520,108 | 5/1985 | Yoshida et al. | 436/52 |
| 4,526,754 | 7/1985 | Burns et al. | 422/82 |
| 4,601,881 | 7/1986 | Webster | 422/67 |
| 4,645,647 | 2/1987 | Yoshida et al. | 436/52 |
| 4,773,446 | 9/1988 | Farnsworth et al. | 137/606 |
| 4,848,722 | 7/1989 | Webster | 251/61.1 |
| 4,852,851 | 8/1989 | Webster | 251/61.1 |
| 4,853,336 | 8/1989 | Saros et al. | 436/53 |
| 4,858,883 | 8/1989 | Webster | 251/61.1 |
| 4,867,201 | 9/1989 | Carten | 137/625.18 |
| 5,045,473 | 9/1991 | Cassaday et al. | 436/53 |
| 5,149,658 | 9/1992 | Cassaday et al. | 436/53 |
| 5,265,843 | 11/1993 | Kleinhappl | 251/129.17 |
| 5,391,353 | 2/1995 | Graffunder | 422/103 |

OTHER PUBLICATIONS

Manning, J.R. "Fluidic Control Devices and Systems". *Fluidics Quarterly,* ca. 1970.

Ohnstein, T. et al. "Micromachined Silicon Microvalve", IEEE Micro Electro Mechanical Systems, Napa Valley, CA, Feb. 11–14, 1980, pp. 95–98.

METHOD AND APPARATUS FOR METERING A FLUID

This application is a File Wrapper Continuation of application Ser. No. 08/334,902 filed Nov. 7, 1994, now abandoned.

BACKGROUND OF THE INVENTION

Embodiments of the present invention relate generally to a method and an apparatus for metering or measuring a determined amount of a fluid and in some instances, combining the metered fluid with another fluid. More specifically, the embodiments relate to a method and an apparatus which meter and in some instances combine fluids in an automated medical or diagnostic instrument.

Medical or diagnostic instruments may be highly complex machines. These instruments may perform tests on fluid samples, such as blood and the like. Such instruments may include a sample receiving area, a sample and reagent admixing area, an incubation area, and a reaction detection area. Each of these areas may perform a specific function or part of a diagnostic test. To do this, each area is supplied with its requirements by a support network. In some instances, these instruments may add fluid to the samples to produce a reaction which generates, directly or indirectly, information regarding the status of the sample. In these cases, the relevant areas of the instruments are supplied with fluid by a fluid network, which may comprise a series of tubes, pressure sources and valves. The fluid network measures the amount of fluid to be added to a sample.

For example, a given instrument may perform a serum analysis. The instrument adds a predetermined volume of one or more reagents to a predetermined volume of a sample of serum. During an incubation period reagent may react with the serum sample. Because of the reaction between sample and reagent, a detectable electromagnetic signal or light may be measured from the reaction mixture in proportion to an item being sought in the sample. A detector in the instrument quantitatively converts the light from the reaction mixture to an electronic signal. Appropriate elements of the instrument, such as a computer and the like, interpret the electronic signal and provide an operator with information about the item sought in the serum sample.

In order for this instrument to perform as intended and to give accurate and repeatable results, it is desirable that a specific, predetermined amount or volume of reagent be mixed with a specific, predetermined volume of the sample. The accuracy and repeatability with which the fluid volumes are metered and combined has a direct effect on the accuracy and repeatability of the measured results the instrument reports to an operator.

The possibility of inaccurate or unrepeatable information being given by an instrument is a concern. Illustrating further by the example of a serum analysis, the test performed may be to see if a unit of blood contains the Hepatitis B virus or antibody to the AIDS virus. Assuming that the blood is infected with the Hepatitis B virus, error in metering and combining either the sample or reagents can result in error in the detected result. This can result in the instrument telling the operator that the unit of blood is not infected with the Hepatitis B virus.

One fluid metering and dispensing apparatus used in diagnostic instrumentation is the positive displacement pump which is connected by a fluidic network of valves and tubing to an aspiration and dispensing tip. This type of fluid metering system aspirates sample, and/or diluent, and/or reagent in open air from sample tubes or reagent bottles and meters them into incubation wells.

Although this type of metering and dispensing system has been developed over years to perform diagnostic tests with benchmark repeatability and accuracy, there may be undesirable characteristics of these systems. One such undesirable characteristic is the use and subsequent accumulation of plastic disposable cuvettes and reagent packaging as a result of performing the diagnostic tests. Another is the potential these systems have for generating disease laden aerosols. Yet another is the difficulty these systems have in assuring the operator that all metering and combining procedures have been carried out as expected. And still another is the difficulty "open air" metering and dispensing has in minimizing the effect of evaporation on repeatable and accurate testing.

Closed fluid handling systems offer potential advantages to solving these problems. Such systems may reduce plastic disposables, aerosol generation, and evaporation. However, to perform comparably they should also be able to provide comparable accurate and repeatable metering and mixing functions for a wide range of fluid volumes.

Accordingly, it can be appreciated that it is desirable, in a closed fluid network in an instrument, to have an element in the instrument which can meter, and in some cases combine, sample, reagents, diluent or other fluids in an accurate and repeatable manner. Furthermore, it can also be appreciated that it is desirable to have elements which provide a wide range of fluid volumes accurately and repeatably, and which provide a reliable form of feedback to assure that metering of fluid and in some cases combining of fluid has occurred.

SUMMARY OF THE INVENTION

Embodiments disclosed involve methods and constructions for metering and in some cases combining fluids. One such method includes fluidly connecting a source of first fluid to be metered with a pressure source capable of moving the first fluid with a first valve and a conduit. The first valve is operated such that first fluid moves in the conduit. The conduit is fluidly connected with a source of second fluid that has a fluid flow rate greater than the first fluid with a second valve. The second valve is operated such that the second fluid moves into the conduit. One construction for metering a fluid comprises a source of first fluid to be metered, a pressure source for moving the first fluid to be metered, and a first valve. A conduit fluidly connects the source of first fluid, the pressure source for moving the first fluid and the first valve such that operation of the first valve causes movement of the first fluid responsive to the pressure source. A second valve fluidly connects a source of second fluid that has a greater fluid flow rate than the first fluid with the conduit such that operation of the second valve causes movement of the second fluid into the conduit.

According to another embodiment, a method for metering a fluid comprises fluidly connecting a source of fluid to be metered with a first valve and a conduit. The first valve is operated such that the fluid moves in the conduit. The first valve is then operated to define a first end of the fluid to be metered. A second valve fluidly connected with the conduit is operated to define a second end of the fluid to be metered.

In another embodiment, a source of first fluid to be metered is fluidly connected with a pressure source capable of moving the first fluid with a valve and a conduit. The valve is operated such that first fluid moves in the conduit. The valve is operated to fluidly connect the conduit with a source of a second fluid that has a greater fluid flow rate than the first fluid.

In yet a further embodiment, at least one of appositive or negative displacement pump is fluidly connected with a source of first fluid to be metered with a conduit containing a second fluid that the first fluid is metered into or to be mixed with the first fluid. Operation of the pump is positively controlled to move a predetermined volume of first fluid from the source of first fluid to be metered into the conduit. The first fluid to be metered is contacted with the second fluid within the conduit to provide desired mixing or seeding of the first fluid and the second fluid.

An additional embodiment provides a construction for metering a fluid including a source of first fluid to be metered, a valve and a conduit fluidly connecting the valve with the source of first fluid. A pressure source capable of moving the first fluid is fluidly connected with the conduit through the valve. A source of second fluid that has a greater fluid flow rate than the first fluid is fluidly connected with the conduit through the valve.

Another embodiment offers a construction comprising a source of first fluid to be metered, a pressure source for moving the first fluid to be metered, a first valve and a conduit fluidly connecting the source of first fluid, the pressure source for moving the first fluid and the first valve such that operation of the first valve causes movement of the first fluid responsive to the pressure source. A source of second fluid that has a greater fluid flow rate than the first fluid is fluidly connected with the conduit by a second valve such that operation of the second valve causes movement of the second fluid into the conduit.

In still another embodiment, a method for metering a fluid includes fluidly connecting a source of fluid to be metered to a conduit through a valve such that fluid to be metered moves in the conduit. Another source of fluid is fluidly connected to the conduit through the valve. A pressure differential between the source of fluid to be metered and the another source is created such that fluid from the another source moves in the conduit instead of the fluid to be metered.

A further embodiment provides a method of metering a fluid. This method involves fluidly connecting a source of fluid to be metered to a conduit through a valve such that fluid to be metered moves in the conduit. Another source of fluid is fluidly connected to the conduit through the valve. A flow rate differential between the fluid to be metered and the fluid from the another source is created such that fluid from the another source moves in the conduit instead of the fluid to be metered.

DETAILED DESCRIPTION OF PREFERRED EMBODIMENTS

While embodiments of the invention are disclosed herein in detail, it is to be remembered that the disclosed embodiments are examples only. Other embodiments are also possible. For instance, it is possible to select and to combine certain elements of a number of embodiments to arrive at other constructions for metering a fluid. While the embodiments are disclosed herein with respect to particular constructions of valves, conduits, etc., for the sake of clarity, it is to be remembered that other similarly functioning elements may be substituted for the disclosed structures without departing from the intended scope of the claims. The embodiments may be used with any suitable fluid. However, it is desirable that materials comprising elements of the system should be compatible with the fluids involved. Additionally, the embodiments may be disposed in a fluid circuit block, viz. a fluid circuit formed from a body and a flexible member. In such a circuit, conduits may be formed as channels on the block.

Figure 1:
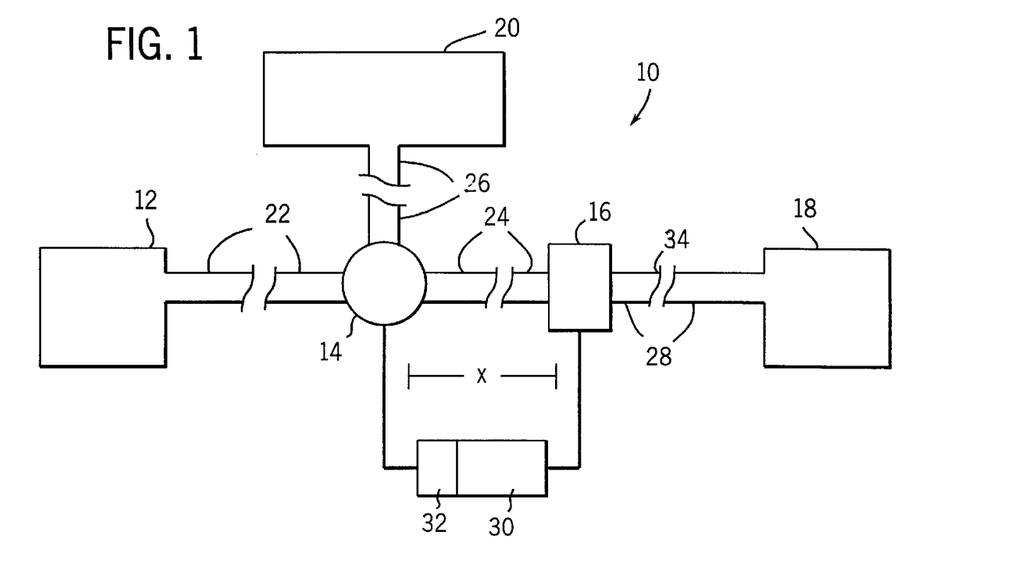
FIG. 1 is a schematic view of one embodiment of the invention for metering an amount of a fluid.

FIG. 1 illustrates a construction 10 for measuring or metering an amount of a fluid. The construction 10 comprises a source 12 of fluid to be metered, a valve 14, a detector 16, a source 18 of relatively reduced pressure and a source 20 of a secondary fluid. The pressures provided by the sources 12, 20 and 18 are predetermined such that there is a pressure differential therebetween such that fluid flows from the source 12 towards the source 18 when sources 12 and 18 are fluidly connected and similarly from source 20 towards the source 18 when sources 20 and 18 are fluidly connected. The fluids in the sources 12 and 20 are chosen such that the fluid in the source 20 has a greater fluid flow rate than the fluid in the source 12.

In this embodiment, fluid is essentially moved or "drawn" from the source 12 toward the source 18. In an alternative embodiment, the fluid may be moved or "pushed" from the source 12 by the source 18. In this alternative embodiment, the source 18 may contain a fluid under a relatively increased pressure appropriately operatively coupled with the source 12. For instance, the source 12 may be operatively positioned in series between the source 18 and the valve 14. In such a case, when the valve 14 is operated properly, the relatively increased pressure fluid from the source 18 can "push" fluid from the source 12 toward the valve 14. Thus, it is to be remembered that any of the embodiments discussed herein may be modified by changing the relatively reduced pressure to a relatively increased pressure and appropriately modifying the structure of the embodiments.

Referring again to FIG. 1, the source 12 contains any desirable fluid to be metered and is fluidly connected to the valve 14 by a conduit 22. The valve 14 is fluidly connected to the detector 16 by conduit 24 and is fluidly connected to the source 20 by conduit 26. The detector 16 is fluidly connected to the source 18 by a conduit 28. The conduits 22, 24, 26 and 28 allow for fluid transfer among the elements of the construction 10 as will be discussed in detail below.

The source 12 may be a fluid container, a port for receiving a fluid container or other structure for supplying a fluid to be metered to the construction 10. The source 18 of reduced pressure may be a sump under vacuum from a vacuum pump, a positive or negative displacement pump, a port for receiving appropriate pressure, and the like. The source 18 provides sufficient reduced pressure to the construction 10 to draw fluid from the source 12 into the conduit 24 when the valve 14 is appropriately operated. In some embodiments, the source 18 provides a pressure to the construction 10 which is lower than the pressure provided to the construction 10 by the source 20. In an exemplary embodiment, the source 18 may provide a vacuum of about 5 to about 10 inches of mercury relative to source 12 to the construction 10, while the source 20 may provide a fluid at a positive pressure of about 5 psi relative to source 12. In other embodiments, the source 20 may be an access to a fluid at ambient pressure. The pressures may be provided by any suitable fluid, such as a gas, a liquid and the like.

Generally, as will become more clear later, it is desirable that the fluid flowing from source 20 and conduit 26 into conduit 24 have a fluid flow rate greater than the fluid flow rate of fluid from source 12 and conduit 22 into conduit 24. In this way, in suitable circumstances, fluid from source 20 flows into conduit 24 more readily than fluid from source 12. This flow rate differential may be accomplished in a number of ways.

One way of providing the above-discussed flow rate differential is to have the flow of fluid from source 20 and conduit 26 into conduit 24 offer less fluid dynamic resistance than the flow of fluid from source 12 and conduit 22 into conduit 24. This resistance difference may be provided by choosing the fluids provided by the sources 12 and 20 such that the fluids appropriately differ in viscosity and/or surface tension. Alternatively, the configurations of the conduits 22 and 26, including the construction of connections between the conduits 22 and 26 and the valve 14, in some cases, may be predetermined to produce the desired fluid dynamic resistance difference or flow rate differential. Other ways, such as combination of the above-described ways, of producing the fluid flow rate differential are also possible. For instance, the fluid dynamic resistance difference, along with pressures applied to the sources 12 and 20, determine that, when both conduits 22 and 26 are fluidly connected to the conduit 24 through valve 14, a majority of fluid flowing into conduit 24 comes from source 20 through conduit 26 instead of from source 12 through conduit 22. In still other embodiments, selection of flow of fluid from source 12 or source 20 may be determined by applying an appropriate pressure differential to the sources 12 and 20 to generate fluid flow.

The valve 14 may be of any suitable construction that allows selection of fluid communication between conduit 22 and conduit 24, between conduit 26 and conduit 24 or among conduits 22, 26 and 24. In an exemplary embodiment, the valve 14 may be a flow-through valve comprising a flow-through channel, a side channel and a fluidly, such as pneumatically and the like, actuated flexible member which controls fluid communication between the flow-through channel and the side channel. In another embodiment, the valve 14, and thus the construction 10, may be incorporated into a fluid circuit. In other embodiments, the valve 14 may fluidly disconnect conduits 22 and 24, fluidly connect conduits 24 and 26 and vice versa. In still further embodiments, the valve 14 may open a juncture between conduits 22 and 24 to a fluid, such as air, under ambient pressure. In this case, because the ambient pressure fluid has a greater fluid flow rate or offers less fluid dynamic resistance than the fluid from the source 12, the ambient pressure fluid would flow into the conduit 24 instead of the fluid from the source 12.

In an exemplary embodiment, the detector 16 is intended to sense a front of a fluid flowing through the conduit 24. The detector 16 may be of any suitable construction. For example, the detector 16 may be an optical system comprising a light emitting diode, a phototransistor and the like. In some embodiments where the detector 16 is electronic, the detector 16 may be electrically connected to a controller 30. The controller 30 may be operatively connected to the valve 14 by a suitable mechanism, such as a transducer, a pneumatic system and the like. The controller 30 operates the valve 14, thereby selecting fluid connection between conduit 24 and either conduit 22 or conduit 26 or both, responsive to sensing of the fluid front by the detector 16. In this way, operation of the valve 14 assists in metering fluid.

To further control operation of the valve 14, in some embodiments, the controller 30 may comprise a timer 32, such as a programmable timer number NE555 available from SIGNETICS of Sunnyvale, Calif. The timer 32 can be programmed to provide a time delay between sensing of the fluid front by the detector 16 and operation of the valve 14. If the source 18 were to provide a substantially constant pressure, and if the fluid to be metered were to have a substantially constant and uniform temperature, viscosity and surface tension, then the metered volume may be a characterizable function of the length of the time delay. By appropriately choosing the length of the time delay, a desired amount of fluid to be metered can be selected. In other embodiments, the controller 30 may comprise a computer executing suitable routines. In further embodiments, a flow-rate measurement device may be included between valve 14 and detector 16 to help determine the time delay. Such a flow-measuring device could consist of two optical detectors spaced a predetermined distance apart with the controller 30 measuring the amount of time the fluid front takes to move from one detector to another.

The conduits 22 through 28 are of suitable construction to accommodate fluids to be conveyed. The conduits 22 through 28 may be of any desirable dimensions. In some embodiments, the dimensions of the conduit 24 between the valve 14 and the detector 16, indicated by "x" in FIG. 1, may be predetermined such that a desired amount of fluid to be metered is disposed within the conduit 24 when the associated fluid front is sensed by the detector 16. Although this is not necessary, it can be appreciated that this embodiment may reduce the sensitivity of this metering method to temperature, viscosity and surface tension and thus improve accuracy and repeatability.

With the structure of the construction 10 being thusly described in detail, the operation of the construction 10 will now be discussed. It is to be noted that further structural details of the construction 10 may be gained by reference to the following discussion of its operation.

To clarify understanding, it is assumed that, initially, the valve 14 is disposed such that the conduit 22 fluidly communicates with the conduit 24. The reduced pressure provided by the source 18 draws fluid to be metered from the source 12 through the conduit 22 towards the valve 14. The fluid to be metered flows past the valve 14 and into the conduit 24. After sufficient fluid has passed the valve 14, the front of the fluid to be metered approaches the detector 16.

The detector 16 senses, such as by measuring attenuation of transmitted light intensity, index of refraction change, internal reflection properties of the conduit 24, conductivity or dielectric property change and the like, the fluid front and generates a signal which is sent to the controller 30. In some embodiments, the controller 30, immediately upon receipt of the signal from the detector 16, operates the valve 14. In these embodiments, the dimensions of the conduit 24 are predetermined to correspond to the desired volume of fluid to be metered. The valve 14 fluidly connects the conduit 24 with the conduit 26 such that the fluid having a greater fluid flow rate or offering less fluid dynamic resistance (source 20) flows into the conduit 24. In other embodiments, a valve may be provided associated with source 12 to positively stop fluid flow from the source 12.

The desired metered volume of fluid from the source 12 is defined by the fluid front which was sensed by the detector 16 and an interface between the fluid to be metered and the fluid from the source 20. The fluid from the source 20 enters the conduit 24. In some embodiments, after a predetermined time interval, the valve 14 can be operated by the controller. By operating the valve 14 again, it is possible to meter another volume of fluid from source 12. In this manner, two metered volumes of fluid from source 12 can move through conduits 24 and 28 separated by a volume of fluid from source 20. Thus, it is desirable that the fluid supplied by source 20 not react with the fluid from source 12.

In still further embodiments, it is possible that the valve 14 may be operated by the controller 30 such that, after the desired volume of fluid from source 12 has been metered, the valve 14 may fluidly connect conduit 24 with another source (not shown) of fluid.

In an exemplary embodiment, the fluid from source 12 may comprise blood and the fluid from the other source may comprise a blood diluent. It is possible to use the same fluid metering construction to meter a blood sample and a blood diluent. The volume of blood sample may be separated from the volume of blood diluent by a volume of fluid, such as air, from the source 20. This preserves separation of the blood and blood diluent until they are ready to be mixed. Of course, in this case, the fluid from source 20 would be chosen such that it would not react with the fluid from source 12 or the other source. Generally, if it were desired to bound a volume of a given fluid by air, then the volume would be moved adjacent a valve fluidly connected to a source of reduced pressure and a valve which vents to air (i.e. a vent valve). By appropriately operating the valves, a desired amount of air can be drawn through the vent valve into the fluid containing conduit by the reduced pressure. It is also possible to choose the fluid from source 20, or from the another source, to remove deposits of fluid from the source 12 from the conduits. It is to be remembered that the flexibility of the construction 10, evident from the above examples, and the other embodiments described herein allows the embodiments to be used in many types of fluid-handling procedures.

In still other embodiments, when the controller 30 receives the signal from the detector 16, the timer 32 begins counting a predefined temporal interval. After the predefined interval has lapsed, the controller 30 operates the valve 14. Once the valve 14 has been operated, things proceed as described above. In these embodiments, viz. with a programmable timer 32, it is possible to vary the amount of fluid metered. For example, a calibrator, which performs analytical tests, such as gravimetric, colorimetric, electrochemical and the like, to measure the amount of fluid metered may be located at point 34 on conduit 28. By measuring the amount of fluid metered with the calibrator and by varying the length of the temporal interval by appropriately programming the timer 32, the same construction 10 can be used to meter various volumes of fluid. Put in another way, the volume of fluid metered can be dependent on the time interval between sensing of the fluid front and operation of the valve 14 and may be independent of the dimensions of the conduit 24.

In any embodiment of the construction 10, after a first volume of fluid has been metered, the valve 14 may be operated again thereby fluidly connecting the conduits 22 and 24, as discussed above. In some embodiments, valve 14 operation may be monitored by the controller 30. Thus, the construction 10 may be used to continually meter fluids. Each metered portion of fluid is defined by a sensed fluid front and an interface between the fluid to be metered and the fluid from the source 20. Thus, multiple metered portions may be separated by fluid from the source 20, as discussed in detail above.

In some embodiments, a receptacle, such as a dilution vessel and the like, may be located at point 34. Relatively large volumes of fluid can be metered by the construction 10 and deposited into the receptacle. These relatively large volumes may comprise a plurality of smaller metered volumes, separated as described. The receptacle may also be a mixing vessel.

Figure 2:
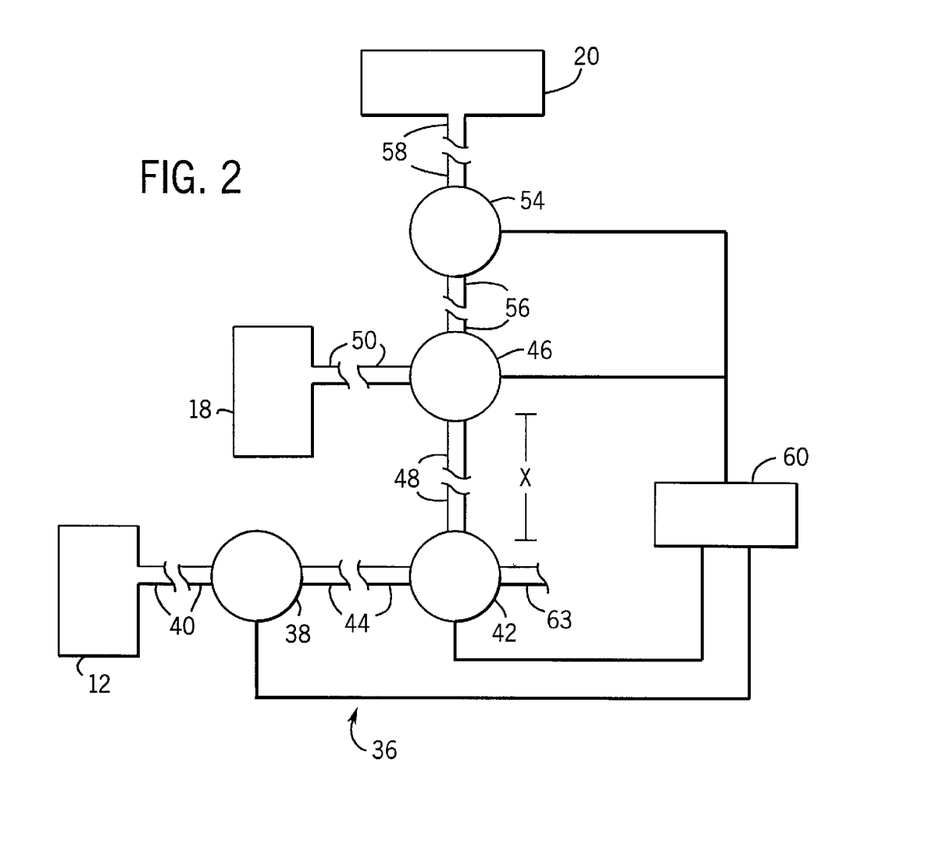
FIG. 2 is a schematic view of another embodiment for metering fluid.

Another construction 36 for metering fluid is shown in FIG. 2. Here, the source 12 of fluid to be metered is fluidly connected to a valve 38 by conduit 40. Valve 38 is fluidly connected to valve 42 by conduit 44. Valve 42 is fluidly connected to valve 46 by conduit 48. Valve 46 is fluidly connected to the source 18 of reduced pressure by conduit 50. Valve 46 is also fluidly connected to a valve 54 by conduit 56. The source 20 of fluid having a fluid flow rate greater than the fluid in source 12 is fluidly connected to valve 54 by conduit 58. Operation of all of the valves 38, 42, 46 and 54 is governed by a controller 60 operatively connected with the valves. The controller 60 may be similar to the controller 30 and may comprise a computer executing appropriate routines, pneumatic systems, transducers, etc.

In an exemplary embodiment of the construction 36, valve 42 is a flow-through valve whose side channel is connected to conduit 48. Valve 46 is a flow-through valve whose side channel is connected to conduit 50. The dimensions of conduit 48, represented by "x" in FIG. 2, are predetermined to correspond to the volume of fluid desired to be metered. Because the conduit 48 determines the amount of fluid to be metered, it is important to know when the conduit 48 is filled with fluid to be metered. This knowledge may be obtained empirically, i.e. the time period needed to fill the conduit 48 may be obtained by visual observation, possibly with the aid of a dye to render the fluid more visible. Alternatively, a detector, similar to the detector 16 may be provided at an appropriate location, such as adjacent the valve 46, near the conduit 48. In this case, the detector would be operatively connected with the controller 60. It is also to be understood that the construction 36, as well as all embodiments described herein, has similar flexibility as the construction 10, described earlier.

Illustrating further by operational example, it is assumed that all valves are closed. The controller 60 operates valves 46, 42 and 38 such that the source 18 is fluidly connected with the source 12. The pressure differential between sources 12 and 18 causes fluid to be metered to flow from the source 12, through the conduit 40, the valve 38, the conduit 44, the valve 42, the conduit 48 towards the valve 46. Of course, the fluid flow may be generated by a relatively increased pressure or a relatively reduced pressure, i.e. "push" or "pull". Fluid may pass through the valve 46 and enter the conduit 50 and/or the conduit 56.

Once the fluid to be metered has filled the conduit 48, the controller 60 operates the valve 42, thereby fluidly disconnecting the conduit 44 from the conduit 48. No further fluid flows into the conduit 48 from the source 12. Operation of the valve 42 causes the valve 42 to define one end of the volume of fluid to be metered.

With the valve 42 being closed, the valve 54 is operated. Since valve 46 is still open, the source 20 is fluidly connected with the conduits 58, 50 and 56. Fluid flow from the source 20 through the conduit 58, the valve 54, the conduit 56, the valve 46 and the conduit 50 replaces fluid from source 12, if present, in the conduit 56 and the conduit 50 with fluid from source 20. Thus, valve 46 forms an end of the metered volume of fluid opposite to the end defined by the valve 42. The controller 60 operates valves 46 and 54. A predetermined volume, corresponding to dimension "x", of fluid from the source 12 is present in conduit 48. The metered volume of fluid may be bounded on an end by another fluid, such as air and the like, from a source. The metered volume of fluid is ready for further processing.

In one embodiment, the controller 60 operates the valve 42 and the metered volume of fluid is drawn towards conduit 63 by suitable means. This may be done after the conduits 40, 44 and 63 are cleaned, such as by passing a suitable fluid from another source through those conduits. Other methods of utilizing the metered volume of fluid are also possible.

Variations of the construction 36 are possible. In one such variation, the conduit 58 fluidly connects the valve 54 to the source 18 and the conduit 50 connects the valve 46 to the source 20. If this were done, the construction would operate as follows.

The controller 60 operates the valves 38, 42 and 54. The valve 46, if it were a flow-through valve, may be open or closed; if it were not a flow-through valve, then the valve 46 would be open, connecting conduit 48 to 56. This fluidly connects the source 12 with the source 18. As before, pressure differential between the sources 12 and 18 causes fluid to flow from the source 12 towards the source 18, thereby filling the conduit 48. It is to be noted that if the valve 46 were a flow-through valve and were open, then the intended fluid flow still occurs. This may be due to a Venturi effect or to a pressure drop across valve 46 experienced by fluid from source 20 but not experienced by fluid from source 12.

The sources 12 and 18 are fluidly connected until the conduit 48 is filled with fluid to be metered. Again, a full conduit 48 may be determined empirically or by using a detector, similar to the detector 16, which may be located near the valve 46 or the valve 54. Fluid flows through the conduit 48 and valve 46 and towards conduit 56. The controller 60 operates the valve 42 such that the sources 12 and 18 are fluidly disconnected. The valve 42 defines one end of the metered volume of fluid. If the valve 46 were a flow-through valve and were open, then any fluid present in the conduits 50, 56 and 58 and the valve 54 is drawn to the source 18. If the valve 46 were a flow-through valve and were closed, it is now opened such that fluid in the conduits 50, 56 and 58 and the valve 54 is drawn to the source 18. Thus, the valve 46 defines an end of the metered volume of fluid opposite to the end defined by the valve 42. The controller 60 operates the valves 46 and 54, leaving the metered volume of fluid within the conduit 48.

Figure 3:
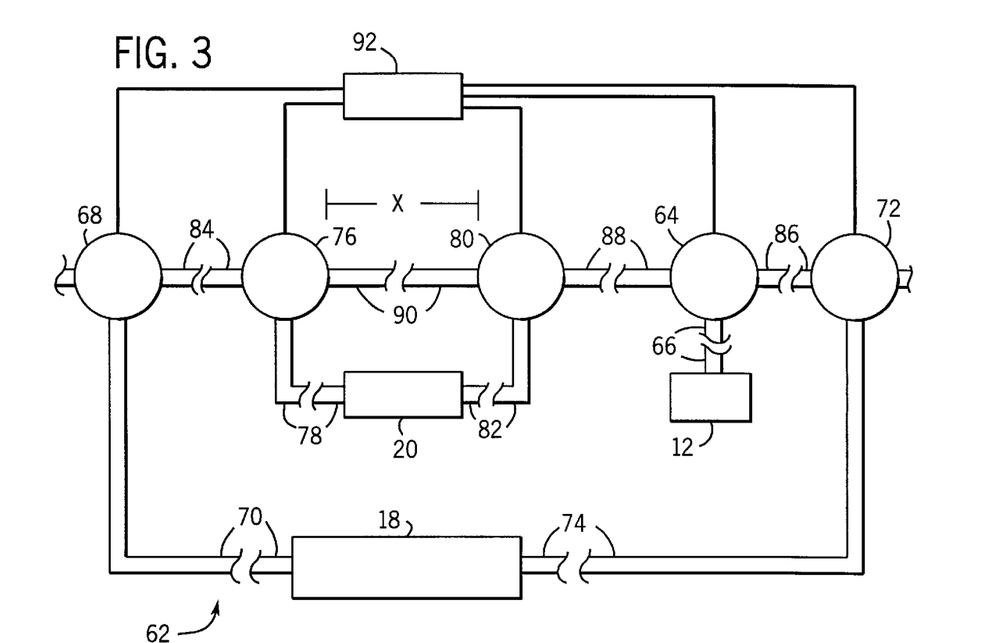
FIG. 3 is a schematic view of an additional embodiment for metering fluid.

Another construction 62 for metering fluid is shown in FIG. 3. The source 12 is fluidly connected to valve 64 by conduit 66. The source 18 is fluidly connected to valve 68 by conduit 70 and to valve 72 by conduit 74. The source 20 is fluidly connected to valve 76 by conduit 78 and to valve 80 by conduit 82. The valves 68 and 76 are fluidly connected by conduit 84, valves 72 and 64 are fluidly connected by conduit 86, and valves 64 and 80 are fluidly connected by conduit 88. Valves 76 and 80 are fluidly connected by conduit 90. In some embodiments, a valve, not shown, such as a shut-off valve and the like, may be fluidly located on conduit 90 between valves 76 and 80. The dimensions, represented by "x" in FIG. 3, of conduit 90 are predetermined to correspond to the desired volume of fluid to be metered. A controller 92, substantially similar to the controllers 30 and 60, is operatively connected to and governs operation of all of the valves 64, 68, 72, 76 and 80.

During operation of the construction 62, the controller 92 operates valves 64 and 68 such that the source 12 is fluidly connected with the source 18. Because of the pressure differential between sources 12 and 18, fluid to be metered flows from the source 12, through conduit 66, valve 64, conduit 88, valve 80, conduit 90, valve 76, conduit 84, valve 68 and conduit 70 toward source 18. The controller 92 operates the valve 76 such that the source 18 is fluidly connected with source 20 through conduit 78, valve 76, conduit 84, valve 68 and conduit 70. Any fluid present in conduit 84 is drawn toward the source 18. An end of the volume of fluid to be metered is defined by the valve 76.

The controller 92 operates the valves 64, 68 and 76, effectively closing those valves. The controller 92 then operates the valves 72 and 80 thereby fluidly coupling the source 20 through conduit 82, valve 80, conduit 88, valve 64, conduit 86, valve 72, and conduit 74 with the source 18. Fluid to be metered present in conduits 86 and 88 and valves 64 and 72 is drawn toward the source 18 through conduit 74. The valve 80 defines an end of the volume of the fluid to be metered opposite to the end defined by the valve 76. The controller 92 operates the valves 72 and 80, effectively closing them. A metered volume of fluid, corresponding to dimension "X", is disposed in conduit 90 and is ready for further processing.

It is to be noted that, in other embodiments, similar to the construction 62, it is possible to fluidly connect source 18 to valves 76 and 80 and to fluidly connect source 20 to valves 68 and 72. Changing sources 18 and 20 in this manner still allows the construction 62 to meter fluid in substantially the same way as described above. However, the direction of fluid flow, as viewed in FIG. 3, within the conduits will be reversed in some locations.

The embodiments may be combined in any desirable fashion to arrive at intended results. For instance, the constructions 10, 36 and 62 may be integrated fluidly. In such a case, the constructions may meter the same fluid or may meter different fluids. The constructions may retain their metered volumes or dispense them into a container to form a mixture. The metered volumes may be dispensed in any order. The combined constructions may be monitored and operated by a single controller.

Figure 4:
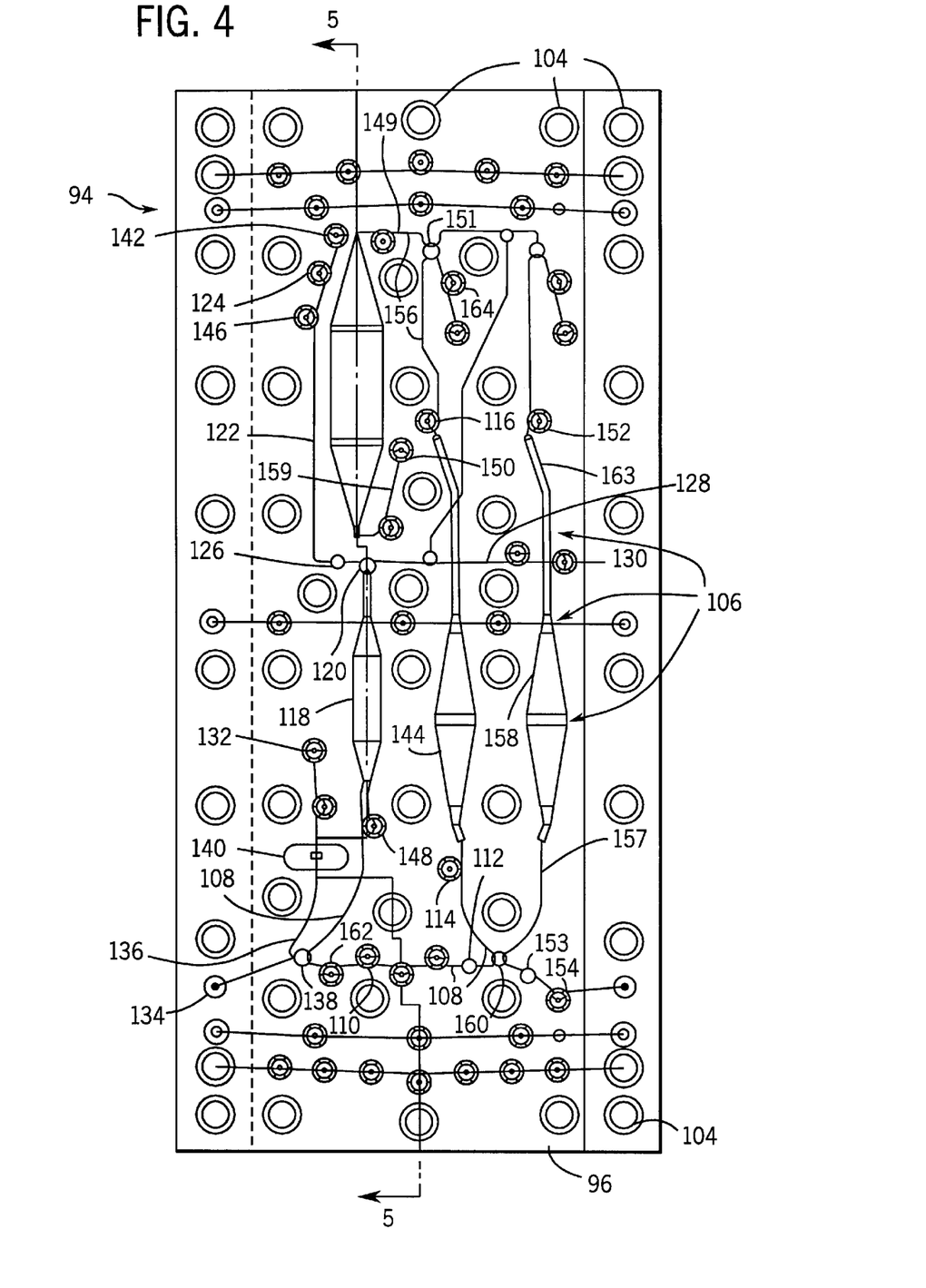
FIG. 4 is a schematic view of a fluid circuit block comprising embodiments for metering a fluid.
Figure 5:
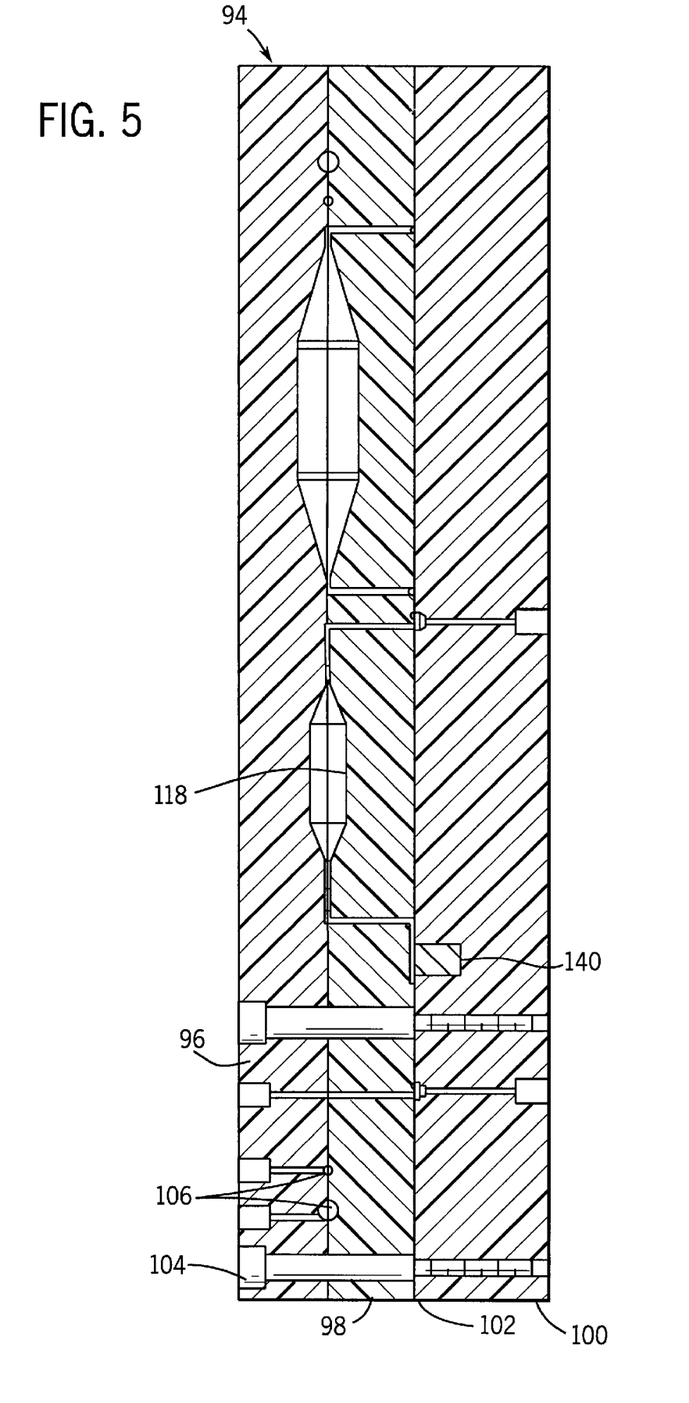
FIG. 5 is a sectional view taken along line 5—5 of FIG. 4.

An example of a combination of embodiments is illustrated in FIGS. 4 and 5. FIGS. 4 and 5 schematically show a fluid circuit block 94 comprising structures for metering a fluid. The fluid circuit block 94 may be formed in any desirable fashion. In the illustrated embodiment, the fluid circuit block 94 comprises a first member 96, a second member 98, a third member 100 and a fourth member 102. In an exemplary embodiment, the first, second and third members, 96, 98, 100 are relatively rigid and the fourth member is relatively flexible. The first, second and third members 96, 98, 100 may be made of a polymer, like a transparent or translucent plastic, such as acrylic and the like. The fourth member 102 may be formed from a polymer, such as Du Pont MYLAR™ and the like. In one embodiment, the first, second and third members 96, 98 and 100 are made from a cast acrylic and the fourth member 100 is made from an about 0.00.05 inch thick piece of Du Pont MYLAR™ including a Flexcon V-95 pressure sensitive adhesive on a side to facilitate bonding of the film to fourth member 100.

The members 96 and 98 are joined together, such as by thermal or ultrasonic welding and the like. The member 100 is joined to the members 96 and 98 by a fastener 104, such as a bolt and the like. The fourth member 102 is held between opposing surfaces of the second member 98 and the third member 100. In other embodiments, the fluid circuit block 94 may be formed from a member having a bore where a fluid valve or fluid actuator may be located. A flexible member is inserted into the bore and held there by a plug also inserted into the bore. In some embodiments, the flexible member may be formed from an elastomer, such as a synthetic rubber (EPDM) and the like.

At least one conduit, generally referenced as 106, is formed on the block 94. In the illustrated embodiment, a plurality of conduits 106 are disposed on the block 94. The conduits 106 may be formed by any suitable technique, such as machining and the like. The conduits 106 may be of any configuration suitable for conveying a desired fluid. As is evident from the above-discussed embodiments, the conduits 106 may have dimensions predetermined to correspond to a desired amount of fluid to be metered. The conduits 106 may be formed at a surface of the members 96, 98 or 100, or may be formed in the interior of the members 96, 98 or 100.

A plurality of valves are associated with the conduits 106. In the illustrated embodiment, some of these valves are flow-through valves. The valves generally comprise a space for allowing fluid flow between at least two conduits. The space is variable by the fourth member 102 which may be actuated fluidly. In one embodiment, a reduced pressure of about 20 inches of mercury relative to ambient is used to flex the fourth member 102 and open a valve whereas a positive pressure of about 20 psig is used to flex the fourth member 102 and close the valve.

Operation of the fluid circuit block 94 is monitored and affected by a controller (not shown) which may be substantially similar to the controllers discussed above. In an exemplary embodiment, the controller may include an electrical control device, a solenoid valve mechanism, and a fluidic connection to a valve. For sake of clarity here the solenoid valve mechanism will be called a pilot valve and the valve in the fluid circuit that it controls will be called a fluid valve. The electrical control device is electrically connected to the solenoid of the pilot valve. In one embodiment, the pilot valve is a Lee Valve Model LHDX0501650A (Westbrook, Conn.). The solenoid controls the pilot valve to fluidly connect a first conduit or a second conduit to a third conduit. The first conduit is fluidly connected to a source of pressure that is lower than both ambient pressure and the relatively reduced pressure source, such as source 18, and preferably offers a vacuum of about 20 inches of mercury. The second conduit is fluidly connected to a source of pressure that is higher than ambient pressure, preferably a pressure of about 20 psig.

The pilot valve fluidly connects either the first or second conduits to the third conduit. Thus, either the relatively reduced pressure associated with the first conduit or the relatively high pressure associated with the second conduit is applied to a fluid valve by means of the third conduit. The pressure applied to the fluid valve determines direction of flexing of the fourth member and thereby opening or closing of the valve.

The electrical control device may comprise any device capable of sending an appropriate signal to the pilot valve. In an exemplary embodiment, the electrical control device may be a programmable microprocessor or computer running suitable routines to control operation of all valves in the block 94. In one embodiment, the computer may be an Apple Macintosh® computer having an MC68030 processor. Such a computer may be interfaced with the pilot valves by a Lab-NB circuit board available from National Instruments of Austin, Tex. The control device may also receive information from detectors in the block 94 and control time delays, discussed above, in valve operation sequences.

Drawing attention to FIG. 4, one of the conduits 106 is conduit 108 which comprises part of a structure for metering a volume of fluid. A fluid supply valve 110 having a side channel coupled with a fluid supply (not shown for clarity) is fluidly connected with the conduit 108. At least one stop valve 112 is also fluidly connected with the conduit 108. One end of the conduit 108 defining the volume of fluid to be metered is defined by a vacuum valve 114 and a vent valve 116. For the purposes of clarity of understanding of this embodiment, it is noted that a vacuum valve operatively connects with a source, such as source 18, whereas a vent valve operatively connects with a source, such as source 20. Another end of the conduit 108 is fluidly coupled with a metering chamber 118. An end of the metering chamber 118 opposite to the end thereof connected to the conduit 108 is fluidly coupled with a valve 120. In the illustrated embodiment, valve 120 is a flow-through valve whose side channel is connected to the metering chamber 118. With this construction, the metered volume of fluid resides within the dimensions of the conduit 108 and the metering chamber 118 between the valve 120 and the vacuum valve 114.

The valve 120 is also fluidly connected with a conduit 122 and a valve 124. In the illustrated embodiment, the valve 124 is a flow-through valve. A pump (not shown for clarity), such as a syringe pump, a positive displacement pump and the like, is fluidly connected to the valve 124. A positive displacement pump allows for further flexibility of the embodiments, as will be discussed in greater detail later. In an exemplary embodiment, the pump is a CAVRO XL3000 syringe pump available from Cavro Scientific Instruments, Inc. of Sunnyvale, Calif. A stop valve 126 is fluidly disposed in the conduit 122 between the valve 124 and the valve 120. Conduit 128 fluidly connects valve 120 to a source (not shown) of relatively reduced pressure, such as source 18, through valve 130.

Further construction of the fluid circuit block 94 will be illustrated by example. It is to be understood that all valves on the block 94 are closed during a given function of the block 94 unless specifically stated otherwise. The block 94 may be integrated with other fluid circuit blocks or may be independent of other fluid circuit blocks. The fluid circuit block 94 may be used in any suitable operation, such as a fluorescence polarization immunoassay, other fluid handling methods and the like.

The controller opens valve 132, which is fluidly connected with a source of reduced pressure. Fluid enters the block 94 through port 134 which is fluidly connected to a source of fluid. The fluid enters conduit 136 which extends between valve 132 and valve 138. Fluid flows into conduit 136 until detector 140 senses the presence of the fluid in the conduit 136. The controller closes valve 132.

The controller opens valve 110, which is fluidly connected to a source of fluid, such as a diluent and the like, and valves 120 and 130. For the sake of clarity, the fluid will be assumed to be a diluent. Metering chamber 118 is filled with diluent. Valve 110 and valve 120 are closed.

Valve 142, connected to a source of fluid, such as diluent and the like, is opened along with valve 126. Valve 130 remains open. The conduits 122 and 128 between valves 142 and 130 are filled with diluent. This diluent may be the same as or different from the diluent discussed above. The controller closes valve 126, valve 130, and valve 142.

The controller opens valve 110, valve 112, valve 114 and valve 116. Diluent flows into conduit 108 and fills conduit 108 between valve 110 and valve 114. The controller closes valves 110, and 112.

The controller leaves valve 114 and valve 116 open for a predetermined time. This removes fluid from conduit 108 and mixing chamber 144 between valve 114 and valve 116.

The controller closes valve 114 leaving vent valve 116 open. Portions of conduit 108 and mixing chamber 144 are vented. At this point, the fluid circuit block 94 contains desired volumes of fluid for further processing.

The controller opens valve 124, valve 142, valve 126 and valve 120. The pump associated with valve 124 is operated to reduce backlash in the pump and/or to ensure the pump is directly engaging and correctly metering fluid. For example, the pump may operate a predetermined time period, or predetermined number of stepping motor steps, sufficient to aspirate a predetermined volume of fluid, which could be about 3 µl. Fluid (diluent) may be moved from conduit 122 toward the pump. A period of time lapses sufficient for fluid motion to stop.

Valve 124, valve 146 (vent), valve 126 and valve 120 are opened. This substantially equalizes pressure within the conduit 122 and the pump. At this point the pump should be capable of directly aspirating accurate and repeatable volumes of fluid through valves and conduits with which it may be fluidly connected.

The controller opens valves 124, 126, 120 and 138. Upon actuating valve 138, diluent in conduit 108 and fluid to be metered in conduit 136 are brought into contact in the valve 138 without any other fluid between those fluids. At this point, fluid is, in some embodiments, present all the way from the pump through valve 124, conduit 122, valves 126, 120, conduit 108, chamber 118, and valve 138, substantially without any gas inclusions. The pump associated with valve 124 is operated and fluid is moved through port 134 across valve 138 into conduit 108. In an exemplary embodiment, the pump is operated to move a predetermined amount, 17 µl, of fluid from port 134 across valve 138 into conduit 108. The controller determines operation time or a predetermined number of steps of the pump to move the desired amount of fluid across the valve 138. Valve 138 is closed after the desired amount of fluid has been moved.

Valves 124, 126 and 120 remain open. Valve 148 is opened by the controller. Valve 148 is fluidly connected with a source of a fluid, such as a reagent and the like. For the sake of clarity, the fluid will be assumed to be a reagent. The pump associated with valve 124 is operated to move a volume of reagent toward metering chamber 118. In an exemplary embodiment, the controller operates the pump such that 10 µl of reagent moves toward the chamber 118. Valves 120 and 148 are then closed. At this point, metering of desired fluids is complete.

Now, the conduits 122 and 128 between valves 142 and 130 may be washed. In one embodiment, this washing is accomplished by separating a wash fluid with bubbles of air to significantly dilute remnants of fluid previously disposed in a conduit. The gas bubbles, associated with a fluid volume, form fluid/gas interfaces which bridge the walls of the conduit and prevent intermixing between successive wash volumes. In this way, carryover between repeated uses of a conduit can be reduced. To perform this rapid serial dilution, the controller opens valves 126 and 130, and alternately valves 142 and 146. This is done a plurality of times, usually four.

The conduits 122 and 128 are dried. The controller opens valves 146, 126 and 130. These valves 146, 126, 130 are left open for a predetermined time period, substantially within the range of about 0.1 and about 5 seconds. The washing cycle is complete.

Fluid, such as a reagent and the like, is moved from metering chamber 118 to mixing chamber 144. The controller opens valve 150 which is associated with a pump, which may be similar to the pump described above. Valves 151, 112, 120, 126 and 146 are also opened. The pump associated with valve 150 is operated such that fluid is moved from chamber 118 into chamber 144. The duration of operation of the pump may be determined empirically as described above. Alternatively, an appropriate detector may be disposed at an appropriate location adjacent the chamber 144.

Once the fluid is in the chamber 144, valves 150, 151 and 116 are opened to vent the conduit extending between valves 150 and 116.

Conduits 163 and 157 and mixing chamber 158 are purged of fluid. To do this, controller opens valve 152 (vent), valve 153 and valve 154 (reduced pressure).

Fluid is moved repeatedly between mixing chamber 144 and mixing chamber 158. The chambers 144 and 158 are configured to facilitate mixing. To move fluid between chambers 144 and 158, the controller opens valves 150, 151, 152, 160, which fluidly joins chambers 144 and 158. The pump associated with valve 150 is operated, alternately generating relatively increased and relatively decreased pressures, to shift fluid repeatedly between chambers 144 and 158. In an exemplary embodiment, the pump is operated to move about 600 µl of fluid in each cycle. The pump performs at least two cycles leaving the bulk of the fluid in conduit 157 and chamber 158.

To complete mixing, the controller opens valves 150, 151, 116 and 152 to vent the relevant conduits.

Processing of fluid by the fluid circuit block 94 is complete. The fluid so processed can move to other structures for further processing. Accordingly, controller opens valves 152 and 153. Fluid processing elements in the other structures can move processed fluid from the block 94.

To prepare the block 94 for subsequent fluid processing, the controller opens valves 146, 126, 120, 162 (reduced pressure), 116 and 114. This essentially dries the associated conduits.

Valves 126, 120, 162 and 114 are opened. Alternately, valves 142 and 146, and valves 164 (providing fluid, such as diluent and the like) and 116 are opened. This washes the relevant conduits. This is done a plurality of times, six in the exemplary embodiment.

To wash conduit 108 between valves 162 and 114, the controller opens valves 126, 120, 162 and 112. Alternately, valves 142 and 146, and valves 164 and 116 are opened as before.

Controller opens valves 146, 126, 120, 162, 116 and 114 to dry the associated conduits. Controller then opens valves 146, 126, 120, 162, 116, and 112 to dry the conduit 108 between valves 114 and 162.

To vent the appropriate conduits to prepare the block 94 for further fluid processing, the controller opens valves 146, 126, 120 and 116. After a predetermined time period, the block 94 is ready to again execute the steps discussed above with another fluid. It is noted that the time required to perform some of the steps outlined above may be dependent on a number of factors, such as, but not limited to the characteristics of the fluid involved, fluid and ambient temperatures, conduit and valve configurations, magnitudes of pressure differentials, valve construction, etc. In some instances, the predetermined time periods allotted by the controller are determined empirically. In other instances as was noted these times may be determined by monitoring sensors to determine when fluids have been transported to specific locations.

As indicated earlier, use of a positive displacement pump to move fluid within an embodiment disclosed herein increases flexibility and potentially the accuracy and repeatability of the embodiment involved. This flexibility concerns moving fluid by "pushing", viz. moving away from the pump, or "pulling", viz. moving toward the pump. It is to be noted, however, that similar effects can be produced without the use of a positive displacement pump.

Figure 6:
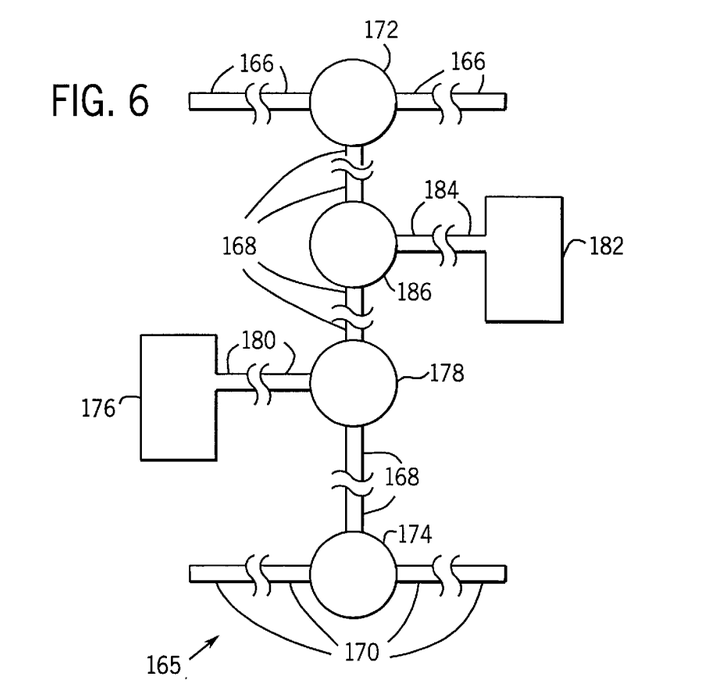
FIG. 6 is a schematic view of another embodiment.

Moving a fluid by pushing or pulling is described with reference to the construction 165 illustrated in FIG. 6. It is to be remembered that other constructions are also possible. Fluid is present in conduits 166, 168 and 170. The fluid in conduit 168 does not have to be the same as the fluid in conduits 166 and 170. Conduit 166 is fluidly coupled with conduit 168 by valve 172 and conduit 168 is fluidly coupled with conduit 170 by valve 174. Conduit 168 is fluidly coupled with a source 176 of fluid through valve 178, located between valves 172 and 174, and conduit 180. It may be desirable that the fluid in conduit 168 not react with the fluid from the source 176. However, in some embodiments, it may be desired that the fluid from source 176 mix with or be diluted by the fluid in conduit 168. In these embodiments, the structures and methods described herein can produce a desired dilution or mixing of fluids in accurate proportions.

A pump 182 is fluidly connected with conduit 168 through conduit 184 and valve 186. Fluid from the source 176 is present in conduit 180. All of the valves 172, 174, 178, 186 are closed. A suitable controller, not shown for the sake of clarity, is provided for monitoring operation of the construction 165.

To pull fluid from the source 176, i.e. move fluid from source 176 towards 182, valves 178 and 186 are opened. The pump 182 is operated thereby inducing a reduced pressure in conduit 168. The controller operates the pump so as to positively control the magnitude of reduced pressure induced in conduit 168, thereby reducing the probability of bubble formation in or outgassing of any fluids in the construction 165.

Fluid from the source 176 is drawn through valve 178. Because the pump 182 is a positive displacement pump, the volume of fluid moved from the source 176 corresponds to the degree of pump operation. Illustrating more clearly by example, if the pump 182 were a syringe pump, then the volume of fluid moved from the source 176 would be proportional to the volume within the syringe formed by movement of the piston. Thus, for a given syringe pump, the volume of fluid moved from the source would be proportional to the distance of movement of the piston. Once the pump 182 operation is complete, valves 178 and 186 are closed. An isolated section of fluid from the source 176 is ready for processing. At no time does any fluid from the source 176 reach the pump 182. If it were desirable that fluid from the source 176 mix with or be diluted by the fluid in conduit 168, then a desired dilution is achieved by these steps.

To push a fluid from the source 176, fluid resides in conduits 166 and 170. Fluid from the source 176 is present in conduits 168 and 180. Another fluid, which does or does not react with the fluid from the source 176, depending upon the particular employment of an embodiment, is present in the conduit 184.

Valves 186 and either valve 172 or valve 174 are opened. The controller activates the pump 182 which induces an increased pressure in conduit 168. The controller monitors operation of the pump 182 such that excessive pressure is not generated thereby reducing the possibility of fluid turbulence and mixing of fluid from the source 176 with fluid associated with the pump 182.

The pump 182 is operated such that fluid from the source 176 is pushed through either valve 172 or valve 174, depending on which one is open. As described above, the volume of fluid moved from source 176 is proportional to operation of the pump 182. Once pump 182 operation is complete, valve 186 and either valve 172 or 174 is closed. A portion of fluid from source 176 is now isolated within either conduit 166 or 170. No fluid from source 176 is moved to pump 182. If it were desirable that fluid from the source 176 mix with or be diluted by the fluid in conduit 166 or 170, then a desired dilution is achieved by these steps.

Given the multiple combinations and variations of the above-discussed embodiments, it is to be noted that the property right associated with these embodiments is limited only by the following claims and their equivalents.

What is claimed is:

1. A method for metering a first fluid, the method comprising the steps of:
    (a) fluidly connecting a source of first fluid to be metered with a pressure source capable of moving the first fluid, the source of first fluid being fluidly connected with the pressure source by a first valve and a conduit;
    (b) operating the first valve such that the first fluid moves in the conduit;
    (c) operating the first valve so that the first valve defines a first end of a metered volume in a first portion of the conduit;
    (d) fluidly connecting the pressure source with a source of second fluid that has a fluid flow rate greater than the first fluid with a second valve and a second portion of the conduit; and
    (e) operating the second valve such that the second fluid moves into the second portion of the conduit simultaneously with movement of the first fluid in the second portion of the conduit to provide said metered volume of the first fluid in the first portion of the conduit with the second valve defining an end of the metered volume of the first fluid in the first portion of the conduit, the metered volume being contained in the first portion of the conduit between the first and second valves.

2. A method as defined in claim 1 further comprising the step of:
    (f) repeating steps (a), (b), (c), (d), and (e) to meter multiple volumes of fluid.

3. A method as defined in claim 1 further comprising the step of:
    (f) bounding the first fluid within the conduit with the second fluid.

4. A method as defined in claim 1 further comprising the step of:
    (f) detecting movement of the first fluid within the conduit.

5. A method as defined in claim 1 further comprising the step of:
    (f) insuring that first fluid does not reach the pressure source.

6. A method as defined in claim 1 further comprising the step of:
    (f) positively controlling operation of the pressure source to reduce at least one of bubble formation in, outgassing of, turbulence in and mixing of first fluid and second fluid.

7. A method as defined in claim 1 further comprising the step of:

(f) positively controlling a time period between operation of the first valve and operation of the second valve.

8. A method as defined in claim 1 further comprising the step of:

(f) predetermining dimensions of the conduit such that the dimensions of the conduit correspond to a volume of fluid to be metered.

9. A construction for metering a first fluid comprising:

(a) a source of first fluid to be metered;

(b) a constant pressure source for moving the first fluid to be metered;

(c) a first valve;

(d) a controller;

(e) a conduit fluidly connecting the source of first fluid, the constant pressure source for moving the first fluid and the first valve, the first valve connected to the controller, wherein the controller operates the first valve to cause movement of the first fluid responsive to the constant pressure source, and the controller operates the first valve so that the first valve defines a first end of a metered volume in a first portion of the conduit;

(f) a source of second fluid that has a fluid flow rate greater than the first fluid; and (g) a second valve fluidly connecting the source of second fluid with the constant pressure source and a second portion of the conduit, the second valve connected to the controller, wherein the controller operates the second valve to cause movement of the second fluid into the second portion of the conduit simultaneously with movement of the first fluid in the second portion of the conduit to provide said metered volume of the first fluid in the first portion of the conduit with the second valve defining an end of the metered volume of the first fluid in the first portion of the conduit, the metered volume being contained in the first portion of the conduit between the first and second valves.

10. A construction as defined in claim 9 further comprising:

(h) a detector operatively associated with the conduit for detecting fluid within the conduit.

11. A construction as defined in claim 9 further comprising:

(h) a timer connected to the controller operatively connected with the first valve and the second valve for monitoring a time period between operation of the first valve and operation of the second valve.

12. A construction as defined in claim 9 wherein the first portion of the conduit has dimensions corresponding to a volume of fluid to be metered.

* * * * *